United States Patent [19]
Hirata

[11] Patent Number: 5,837,483
[45] Date of Patent: Nov. 17, 1998

[54] ENZYMATIC METHOD FOR PRODUCING N-FORMYL-α-L-ASPARTYL-L-PHENYLALANINE METHYL ESTER

[75] Inventor: Akira Hirata, Tokyo, Japan

[73] Assignee: Holland Sweetener Company V.o.F., Maastricht, Netherlands

[21] Appl. No.: 939,949

[22] Filed: Sep. 29, 1997

[30] Foreign Application Priority Data

Oct. 15, 1996 [JP] Japan .................................. 8-272129

[51] Int. Cl.$^6$ .............................. C12P 21/60; C12P 13/04
[52] U.S. Cl. ...................... 435/68.1; 435/70.1; 435/71.1; 435/105; 435/182; 435/185; 435/280; 435/175; 530/344; 530/801
[58] Field of Search ................. 435/68.1, 70.1, 435/71.1, 106, 175, 182, 185, 280; 530/344, 801

[56] References Cited

FOREIGN PATENT DOCUMENTS

| | | |
|---|---|---|
| 0 149 594A | 1/1985 | European Pat. Off. . |
| 60164495 | 8/1985 | Japan . |
| 62259597A | 11/1987 | Japan . |
| 3087195A | 4/1991 | Japan . |

OTHER PUBLICATIONS

Bio/Technology vol. 3 May, 1985, Continuous Synthesis of N–(Benzyloxycarbonyl)–L–Aspartyl–L–Phenylalanine Methyl Ester with Immobilized Thermolysin in an Organic Solvent, K. Nakanishi et al, pp. 459–464.

*Primary Examiner*—Herbert J. Lilling
*Attorney, Agent, or Firm*—Pillsbury Madison & Sutro LLP

[57] ABSTRACT

An enzymatic method for producing N-formyl-α-L-aspartyl-L-phenylalanine methyl ester by a condensation reaction between N-formyl-L-aspartic acid and L-phenylalanine methyl ester or D,L-phenylalanine methyl ester, which comprises: supplying an organic phase comprising a water-immiscible solvent containing N-formyl-L-aspartic acid and L- or D,L-phenylalanine methyl ester onto an aqueous phase comprising a thermolysin-like metalloprotease; proceeding the condensation reaction in the aqueous phase to produce N-formyl-α-L-aspartyl-L-phenylalanine methyl ester; and extracting the N-formyl-α-L-aspartyl-L-phenylalanine methyl ester thus produced from the aqueous phase to the organic phase.

7 Claims, 2 Drawing Sheets

ENZYMATIC METHOD FOR PRODUCING N-FORMYL-α-L-ASPARTYL-L-PHENYLALANINE METHYL ESTER

FIELD OF THE INVENTION

This invention relates to an enzymatic method for producing N-formyl-α-L-aspartyl-L-phenylalanine methyl ester (hereinafter referred to as "F-APM") by a condensation reaction between N-formyl-L-aspartic acid (hereinafter referred to as "F-L-Asp") and L-phenylalanine methyl ester or D,L-phenylalanine methyl ester (hereinafter referred to as "L-PM" and "D,L-PM", respectively).

α-L-Aspartyl-L-phenylalanine methyl ester, namely aspartame, is an intense sweetener having about 200 times sweetness of cane sugar, and can be produced inter alia by removing N-formyl protecting group from F-APM obtained by the condensation reaction of F-L-Asp and L-PM or D,L-PM.

BACKGROUND OF THE INVENTION

As a previous method for producing F-APM by the condensation reaction between F-L-Asp and L-PM, for example, the method of U.S. Pat. No. 3,786,039 wherein F-L-Asp and L-PM are allowed to react in organic solvent was proposed.

However, this method is not a useful method as an industrial process because both of α-isomer and β-isomer are produced, and separation-purification is necessary to remove the useless β-isomer.

As a method to improve the above fault, some enzymatic methods for producing F-APM were proposed. For example, JP-A-60-164495 (the term "JP-A" as used herein means an unexamined published Japanese patent application) shows an example wherein F-APM.PM (1:1 addition product) was produced as a white solid by a condensation reaction between F-L-Asp and L-PM.HCl and use of thermolysin as enzyme. The white solid floated on the water. After the reaction, the pH of the water was adjusted to be 1.6 by addition of hydrochloric acid, and thus-obtained F-APM was extracted to ethyl acetate.

However, in even this method, the yield of F-APM was only 41%, and it may be concluded from this result that the yield of F-APM is strongly limited when the reaction proceeds in an aqueous solution.

As a method to dissolve this fault, a new method for producing N-protected-α-L-aspartyl-L-phenylalaninemethyl ester (hereinafter referred to as "N-protected-APM") wherein said condensation reaction proceeds in reaction system of two-phase consisting of the organic phase in which N-protected-L-aspartic acid and L-PM are dissolved and the water-phase in which a protease is dissolved, and the N-protected-APM produced is transferred to the organic phase as an ammonium salt or phosphonium salt was described in JP-A-62-259597.

However, in even this method, the yield of N-protected-APM is only 20%, and any sufficient effect was not achieved. As to the organic solvent, it was merely described that any organic solvent in which a tertiary ammonium salt or a tertiary phosphonium salt can be dissolved can be used; however, no specific kind of effective organic solvent was described in said patent application.

In order to improve the yield of N-benzyloxycarbonyl-L-aspartyl-L-phenylalanine methyl ester (hereinafter referred to as "Z-APM"), Nakanishi et al. proposed a method in a biphasic system using immobilized thermolysin wherein the organic phase containing N-benzyloxycarbonyl-L-aspartic acid (hereinafter referred to as "Z-L-Asp") and PM is supplied onto the aqueous phase containing immobilized thermolysin to produce Z-APM in the aqueous phase, and the Z-APM produced is immediately transferred from the aqueous phase to the organic phase (ethyl acetate) (BIO/TECHNOLOGY vol. 3, pp. 459–464, 1985).

However, the yield of Z-APM was only about 40% when 1:1 mole ratio of PM and Z-Asp was used as shown in FIG. 2 of p. 460 of this literature.

Besides, effect of organic solvents on the initial ratio of synthesis of Z-APM and the partition coefficient of L-PM, defined as "the ratio of the concentration L-PM in the aqueous phase to that in the organic phase" were shown in Table 1 of p. 461 of this reference. However, only three organic solvents, namely ethyl acetate, 1,2-dichloroethane and chloroform, were investigated, and any partition coefficient of the Z-APM produced as defined as the ratio of the concentration of Z-APM in the organic phase to that in the aqueous phase was not considered and any criterium to select an effective organic solvent for extraction of Z-APM from the aqueous phase into the organic phase was not discussed at all in this reference. Also, there was no description nor suggestion to apply such method for producing F-APM.

Therefore, any method for producing effectively F-APM by the condensation reaction between F-L-Asp and L-PM or D,L-PM wherein said condensation reaction proceeds in aqueous phase and the F-APM produced is transferred to the organic phase by using an extracting agent in the reaction system of two-phase consisting of the organic phase in which N-protected-L-aspartic acid and L-PM are dissolved and the aqueous-phase in which a protease is dissolved has not been proposed till now.

Moreover, when F-APM is produced in industrial scale, a continuous operation is more preferable than a batchwise operation from the point of view of effectiveness and simplicity of operation.

The inventor of this patent application applied a continuous reaction to a method for producing Z-APM by a condensation reaction between Z-L-Asp and L-PM as described in JP-A-3-87195 wherein Z-APM is produced in the inner column of the aqueous phase containing the immobilized thermolysin and the thus-produced Z-APM was transferred simultaneously into the organic phase in the outer column and was outleted to a reservoir of organic solvent.

However, the yield of Z-APM based on Z-L-Asp was only about 70% in even this case.

Nakanishi et al. applied the method described in the previous literature (BIO/TECHNOLOGY vol. 3, pp. 459–464, 1985) to such a continuous process wherein a substrate solution containing 80 mM Z-L-Asp and 200 mM L-PM with 5 mM $CaCl_2$, dissolved in ethyl acetate was fed continuously onto the immobilized enzyme-containing aqueous phase; however, the yield of Z-APM based on Z-L-Asp was gradually decreased to 75% after 185 hours from the start of the condensation reaction between Z-L-Asp and L-PM.

Therefore, there is no need for an efficient continuous method for producing dipeptide esters, especially N-protected-APM, where a protecting group can be used which is less expensive than the benzyloxycarbonyl group as used in the above-mentioned process. The formyl group is less expensive than the benzyloxycarbonyl group.

SUMMARY OF THE INVENTION

This invention was done by considering the problems as described above, and it is an object of this invention to provide a new enzymatic method for producing effectively F-APM by a condensation reaction between F-L-Asp and L-PM or D,L-PM.

Accordingly, in view of the above, the inventors have conducted intensive investigations to solve the problems described previously, and this invention was completed by finding that F-APM can be extracted effectively from an aqueous solution phase to an organic phase by proper selection of water-immiscible solvent.

Accordingly, this invention completed a novel enzymatic method for producing N-formyl-α-L-aspartyl-L-phenylalanine methyl ester by a condensation reaction between N-formyl-L-aspartic acid and L-phenylalanine methyl ester or D,L-phenylalanine methyl ester, which comprises:

supplying an organic phase comprising a water-immiscible solvent containing N-formyl-L-aspartic acid and L- or D,L-phenylalanine methyl ester onto an aqueous phase comprising a thermolysin-like metalloprotease;

proceeding the condensation reaction in the aqueous phase to produce N-formyl-a-L-aspartyl-L-phenylalanine methyl ester; and extracting the N-formyl-a-L-aspartyl-L-phenylalanine methyl ester thus produced from the aqueous phase to the organic phase.

Figure 1:
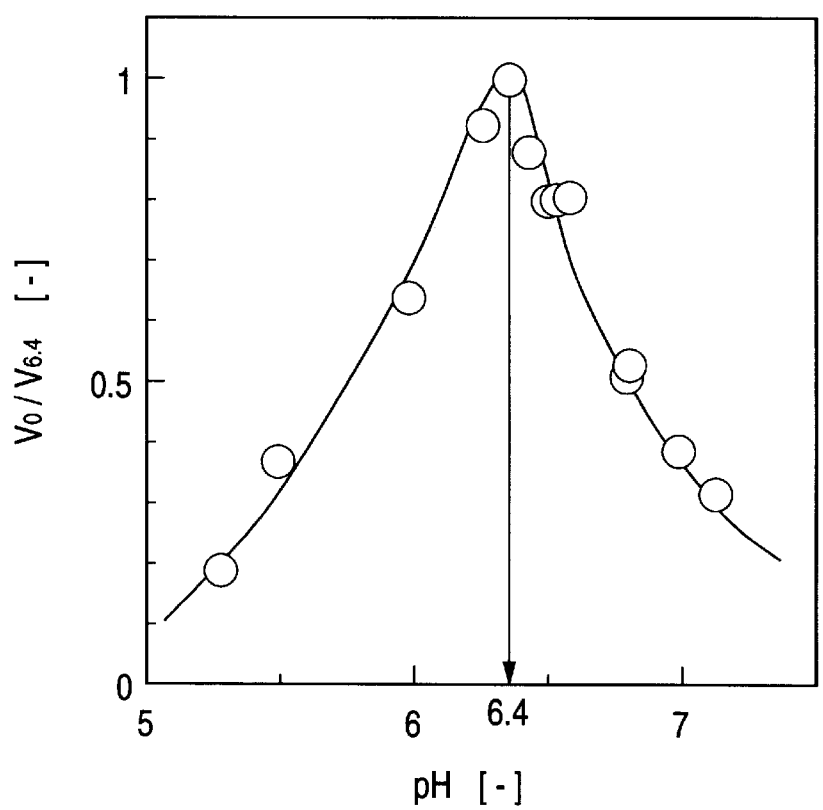
FIG. 1 shows the relationship between an initial rate of F-APM formation and pH.

1: real body of reactor
2: water-jacket
3: stirring blade
4, 5: supply pumps to feed substrate solution containing F-L-Asp and L-PM
6: pH controller
7: supply pump to feed 5N-NaOH for pH adjustment
8: pH electrode
9: settler.

Figure 4:
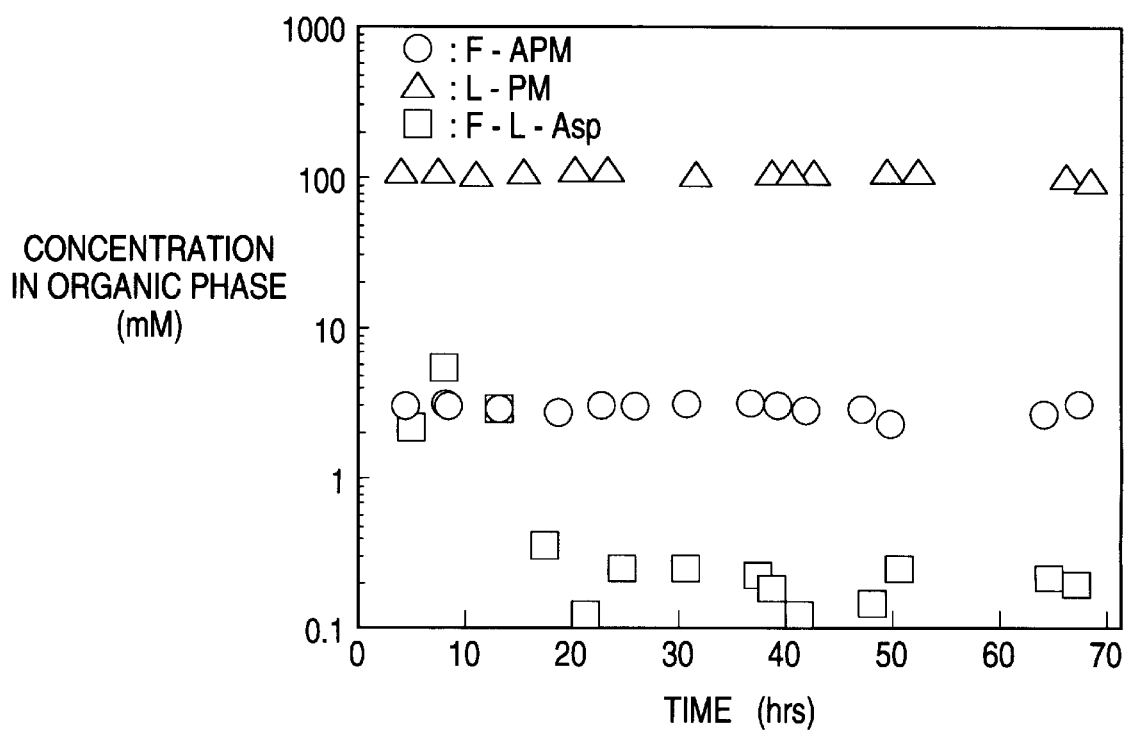

FIG. 4 shows changes of the concentrations of F-APM produced and substrates of F-L-Asp and L-PM in an organic solvent with time when tri-butyl phosphoric acid was used as the organic solvent.

DETAILED DESCRIPTION OF THE INVENTION

The water-immiscible solvents of which distribution ratios ($D_{F-APM}$) described by following equation (1) are $10^{-2}$ or more at pH=6.0 are suitable for effective the extraction of the F-APM produced to the organic phase:

$$D_{F-APM} = \frac{P_{F-APM}}{1 + 10^{pH - pK_{F-APM}}} \quad (1)$$

wherein $$P_{F-APM} = (C_{F-APM})_{org}/(C_{F-APM})_{aq} \quad (1a);$$

$$K_{F-APM} = \{(C_{F-APM^-})_{aq} \times C_{H^+}\}/(C_{F-APM})_{aq} \quad (1b);$$

which $(C_{F-APM})_{org}$: concentration of F-APM contained in the organic phase after the extraction of F-APM;

$(C_{F-APM})_{aq}$: concentration of F-APM remained in the aqueous phase after the extraction of F-APM;

$(C_{F-APM^-})_{aq}$: concentration of F-APM$^-$ remained in the aqueous phase after the extraction of F-APM;

$C_{H^+}$: concentration of H$^+$ remained in the aqueous phase after the extraction of F-APM.

Above $P_{F-APM}$ and $K_{F-APM}$ were obtained by following partition model of F-APM described by following scheme 1.

(Scheme 1)

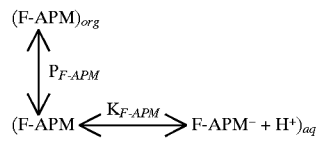

Furthermore, above equation (1) was obtained by relation described by following equation (3).

$$D_{F-APM} = \frac{(C_{F-APM})_{org}}{(C_{F-APM})_{aq} + (C_{F-APM^-})_{aq}} \quad (3)$$

$$= \frac{(C_{F-APM})_{org}}{(C_{F-APM})_{aq}} \times \frac{1}{1 + (C_{F-APM^-})_{aq}/(C_{F-APM})_{aq}}$$

$$= \frac{P_{F-APM}}{1 + (K_{F-APM} \times C_{H^+})^{-1}} = \frac{P_{F-APM}}{1 + 10^{pH - pK_{F-APM}}}$$

Moreover, organic solvents of which distribution ratios of F-L-Asp ($D_{F-L-Asp}$) described by following equation (2) are $10^{-4}$ or less at pH=6.0 are suitable for increase of conversion ratios to F-APM because large amount of F-L-Asp can be distributed in aqueous phase:

$$D_{F-L-Asp} = \frac{P_{F-L-Asp}}{1 + 10^{pH - pK_{F-L-Asp1}} + 10^{2pH - pK_{F-L-Asp1} - pK_{F-L-Asp2}}} \quad (2)$$

wherein $$P_{F-L-Asp} = (C_{F-L-Asp})_{org}/(C_{F-L-Asp})_{aq} \quad (2a);$$

$$K_{F-L-Asp1} = \{(C_{f-L-Asp^-})_{aq} \times C_{H^+}\}/(C_{F-L-Asp})_{aq} \quad (2b);$$

$$K_{F-l-Asp2} = \{(C_{F-L-Asp^{2-}})_{aq} \times C_{H^+}\}/(C_{F-L-Asp^-})_{aq} \quad (2c);$$

which $(C_{F-L-Asp})_{org}$: concentration of F-L-Asp contained in the organic phase after the extraction of F-APM;

$(C_{F-L-Asp})_{aq}$: concentration of F-L-Asp remained in the aqueous phase after the extraction of F-APM;

$(C_{F-L-Asp^-})_{aq}$: concentration of F-L-Asp$^-$ remained in the aqueous phase after the extraction of F-APM;

$C_{H^+}$: concentration of H$^+$ remained in the aqueous phase after the extraction of F-APM;

$(C_{F-L-Asp^{2-}})_{aq}$: concentration of F-L-Asp$^{2-}$ remained in the aqueous phase after the extraction of F-APM.

The $D_{F-L-Asp}$ shows the ability to suppress the transfer (extraction) of F-L-Asp from the aqueous phase.

$P_{F-L-Asp}$, $K_{F-L-Asp1}$ and $K_{F-L-Asp2}$ were obtained by the partition model of F-L-Asp described by following scheme 2:

(Scheme 2)

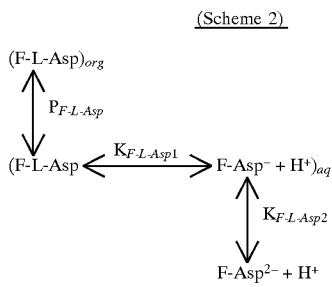

Furthermore, above equation (2) was obtained by following equation (4):

$$
\begin{aligned}
D_{F-L-Asp} &= \frac{(C_{F-L-Asp})_{org}}{(C_{F-L-Asp})_{aq} + (C_{F-L-Asp^-})_{aq} + (C_{F-L-Asp^{2-}})_{aq}} \quad (4)\\
&= \frac{(C_{F-L-Asp})_{org}}{(C_{F-L-Asp})_{aq}} \times \\
&\quad \frac{1}{1 + \{(C_{F-L-Asp^-})_{aq} + (C_{F-L-Asp^{2-}})_{aq}\}/(C_{F-L-Asp})_{aq}}\\
&= \frac{P_{F-L-Asp}}{1 + (K_{F-L-Asp1}/C_{H^+}) + (K_{F-L-Asp1}/C_{H^+})(K_{F-L-Asp2}/C_{H^+})}\\
&= \frac{P_{F-L-Asp}}{1 + 10^{pH-pK_{F-L-Asp1}} + 10^{2pH-pK_{F-L-Asp1}-pK_{F-L-Asp2}}}
\end{aligned}
$$

On the other hand, the organic solvents in which hydrolysis rate of L-PM or D,L-PM used as one of raw materials is high are not preferably, and the hydrolysis rate is closely related to mutual solubility between the organic solvents and water. Namely, the organic solvents of which solubility in water is large are not preferable because hydrolysis rate of L-PM or D,L-PM are large in such organic solvents. Therefore, water-immiscible organic solvents are preferably to be used as a solvent in this invention.

As such water-immiscible organic solvents, the solvents selected from the group consisting of tri-butyl phosphate, n-amyl alcohol, methyl ethyl ketone, 1-butanol, isobutanol and tertiary amylalcohol are preferable because the conversion ratios to F-APM are high in such solvents.

Moreover, extracting agent may be used to improve the extraction efficiency of the F-APM produced, and it is preferable to select ammonium salts and phosphonium salts which are phase-transfer catalysts having strong extracting ability as extracting agents.

Furthermore, any commercial thermolysin-like metalloprotease, for example, thermoase (commercial name, manufactured by Daiwa Kasei Co., Ltd.) can be used as an enzyme used in this invention. As used herein in the thermolysin-like metalloprotease encompasses "wild type thermolysin-like neutral metalloprotease which is coded by nprM, one of the protease genes cloned from *Bacillus stearothermophilus* (Kubo, M., et al., *Journal of General Microbiology*, 134:1883–1892 (1988)) or the gene from *Bacillus stearothermoproteolyticus* (Endo, S., *J. Fermentation Tech.*, 40:346–353 (1962)), and any mutants thereof obtained by replacements of one or more amino acids by other amino acids, or by deletion or by insertion of one or more amino acids in the naturally occurring sequences thereof. All such mutants as encompassed hereby are capable of forming selectively (N-protected)-L-aspartyl-L-phenylalanine methyl ester. Examples of such mutants are modified neutral proteases having the amino acid sequence of above "wild type thermolysin-like neutral metalloprotease" wherein at least one amino acid residue selected from the group consisting of the 144th residue, leucine, the 150th residue, aspartic acid, the 187th residue, glutamic acid, and the 227th residue, asparagine, is replaced with an amino acid residue other than said amino acid residue (EP 0 616 033 Al), especially wherein the 150th residue, aspartic acid, is replaced with tryptophan (WO 95/16029), and mutants wherein the volume of the cavity in electron density existing in the 144th residue, leucine, in the 149th residue, threonine, the 240th residue, alanine, the 270th residue, alanine, and the 288th residue, alanine, is replaced either by filling at least part of said cavity by replacing at least one amino acid residue with one or more hydrophobic and/or more bulky amino acid residues, or by influencing of the amino acid resides confining the cavity of electron density (WO 97/21804). All such metalloproteases have been used in the synthesis of Z-APM which is a precursor of aspartame as described in, for example, U.S. Pat. No. 4,116,768, EP 0 616 033 Al, WO 95/16029 and WO 97/21804.

F-L-Asp and L-PM or D,L-PM may be contained firstly in the water-immiscible solvent, and the organic phase consisting of said water-immiscible solvent may be supplied onto aqueous solution phase, or solid F-L-Asp and solid L-PM or D,L-PM may be supplied onto organic phase and/or aqueous solution phase separately.

A pH range of 6.0 to 6.5 in the aqueous phase is the most preferable from a point of view of reaction kinetic theory, however, such pH range is not always necessary because the extracting rate of the F-APM produced to the organic phase is rate-determining. For example, if the pH is lowered, the conversion ratio to F-APM is raised because the solubilities of L-PM or D,L-PM increase. Therefore, lower pH than 6.0 to 6.5, for example, pH of about 5.0, is preferable, and pH in the aqueous phase should be selected considering balance of extracting rate of F-APM produced and conversion ratio to F-APM.

Moreover, both a batch-wise operation and a continuous operation are available, but a continuous operation is preferable from the point of view of efficiency and simplification of operation, and processes of this invention can be applied to a continuous operation. Namely, a continuous operation wherein an organic phase in which F-L-Asp and L-PM or D,L-PM of raw materials are contained is supplied continuously onto an aqueous phase in which thermolysin-like metalloprotease is dissolved, the F-APM produced is transferred from the aqueous phase to the organic phase, and the organic phase containing the F-APM is taken out continuously is possible.

In this invention, F-APM can be produced effectively by the method of this invention wherein the organic phase comprising a water-immiscible solvent is supplied onto the aqueous phase, the condensation reaction between F-L-Asp and L-PM or D,L-PM is carried out in the aqueous phase and the F-APM produced is transferred efficiently to a specified organic phase, and the method of this invention can be applied to a continuous operation which is preferable from a point of view of efficiency and simplification of operation.

EXAMPLES

This invention will hereinafter be explained by means of examples and comparative examples. However, it should be noted that this invention is by no means limited to these examples.

EXAMPLE 1

Selection of Organic Solvents 10 ml of organic solvent saturated by water and 10 ml of aqueous solution saturated by organic solvent were entered into sample tube, and 50 mM of F-L-Asp was dissolved in said organic solvent saturated by water and 50 mM of F-APM was dissolved in said aqueous solution saturated by organic solvent.

As a value showing the ability of organic solvent to extract F-APM from aqueous phase, $DF$-ApM described by equation (1) were used.

As a value showing the ability to suppress transfer of F-L-Asp from aqueous phase to organic phase, $D_{F-L-Asp}$ described by equation (2) was used.

Measurements of these $P_{F-APM}$ and $P_{F-L-Asp}$ were carried out at 40° C.

$D_{F-APM}$ values of many kinds of organic solvent are shown in Table 1 wherein methyl isobutyl ketone, n-butylformate and butyl acetate are shown as comparative examples, and $D_{F-L-Asp}$ values of many kinds of organic solvent are shown in Table 2.

TABLE 1

| Organic Solvent | $P_{F-APM}$ | $pK_{F-APM}$ | $D_{F-APM}$ pH = 5 | pH = 6 | pH = 7 |
|---|---|---|---|---|---|
| tri-butylphosphoric acid | 13.0 | 4.01 | 1.20 | 0.13 | 0.0133 |
| n-amylalcohol | 3.70 | 4.22 | 0.527 | 0.0604 | 0.0061 |
| t-amylalcohol | 6.89 | 4.21 | 0.866 | 0.107 | 0.0111 |
| 1-butanol | 7.13 | 4.17 | 0.919 | 0.101 | 0.0105 |
| methyl ethyl ketone | 2.14 | 4.61 | 0.556 | 0.087 | 0.0087 |
| methyl isobutyl ketone | 0.80 | 4.01 | 0.074 | 0.0080 | 0.00082 |
| n-butylformate | 0.64 | 4.17 | 0.083 | 0.0091 | 0.0012 |
| butylacetate | 0.47 | 4.02 | 0.045 | 0.0049 | 0.00049 |

TABLE 2

| Organic solvent | $P_{F-A-Asp}$ | $pK_{F-L-Asp1}$ | $pK_{F-L-Asp2}$ | $D_{F-L-Asp} (\times 10^{-4})$ pH = 5 | pH = 6 | pH = 7 |
|---|---|---|---|---|---|---|
| tri-butyl phosphoric acid | 0.558 | 3.18 | 4.44 | 18.2 | 0.226 | 0.00231 |
| n-amylalcohol | 0.166 | 2.95 | 4.17 | 1.9 | 0.0216 | 0.00021 |
| t-amylalcohol | 0.498 | 3.16 | 4.63 | 21.4 | 0.294 | 0.00305 |
| 1-butanol | 0.424 | 2.99 | 4.83 | 16.6 | 0.262 | 0.00278 |
| methyl ethyl ketone | 0.296 | 3.43 | 4.43 | 16.0 | 0.201 | 0.00206 |
| isobutanol | 0.356 | 3.11 | 4.44 | 9.9 | 0.123 | 0.00125 |

It is clear from these tables that the water-immiscible solvents selected from tri-butylphosphoric acid, n-amylalcohol, t-amylalcohol, 1-butanol, methyl ethyl ketone and isobutanol are preferable because $D_{F-APM}$ values at pH=6.0 are $1\times10^{-2}$ or more and $D_{F-L-Asp}$ values at pH=6.0 are $1\times10^{-4}$ or less. Determination the most preferable pH of aqueous phase:

An aqueous solution containing 1 g/l of thermoase (commercial name, manufactured by Daiwa Kasei Co., Ltd.) and a substrate solution in water in which 70 mM of F-L-Asp and 100 mM of L-PM were dissolved and were prepared separately and were maintained at 40° C.

After pH of said substrate solution was adjusted by addition of 1N-NaOH aqueous solution, 5 ml of thus-obtained 1 g/l of thermoase were mixed and the condensation reaction between F-L-Asp and L-PM was started.

Concentrations of F-L-Asp, L-PM and F-APM were analyzed by HPLC.

FIG. 1 shows the relationship between pH and an initial formation rate of F-APM. The axis of ordinates shows a relative value against the initial formation rate of F-APM at 6.4 ($V_{64}$=0.0060 mM/min.).

It is clear that the most preferable pH of the aqueous phase is about 6.4.

EXAMPLE 2

This example was carried out by batchwise operation in biphase system of aqueous phase and organic phase.

An enzyme aqueous solution of pH=6.5 containing 1.131 g/l of thermoase, 0.1M buffer agent (MES) and 0.01M $CaCl_2$, and substrate tributyl phosphoric acid solution containing 88.15 mM of F-L-Asp and 120.97 mM of L-PM were prepared separately and were maintained at 40° C. Both 5 ml's of two solutions were mixed and the condensation reaction between F-L-Asp and L-PM was started. Concentrations of F-L-Asp, L-PM and F-APM were analyzed by HPLC.

Figure 2:
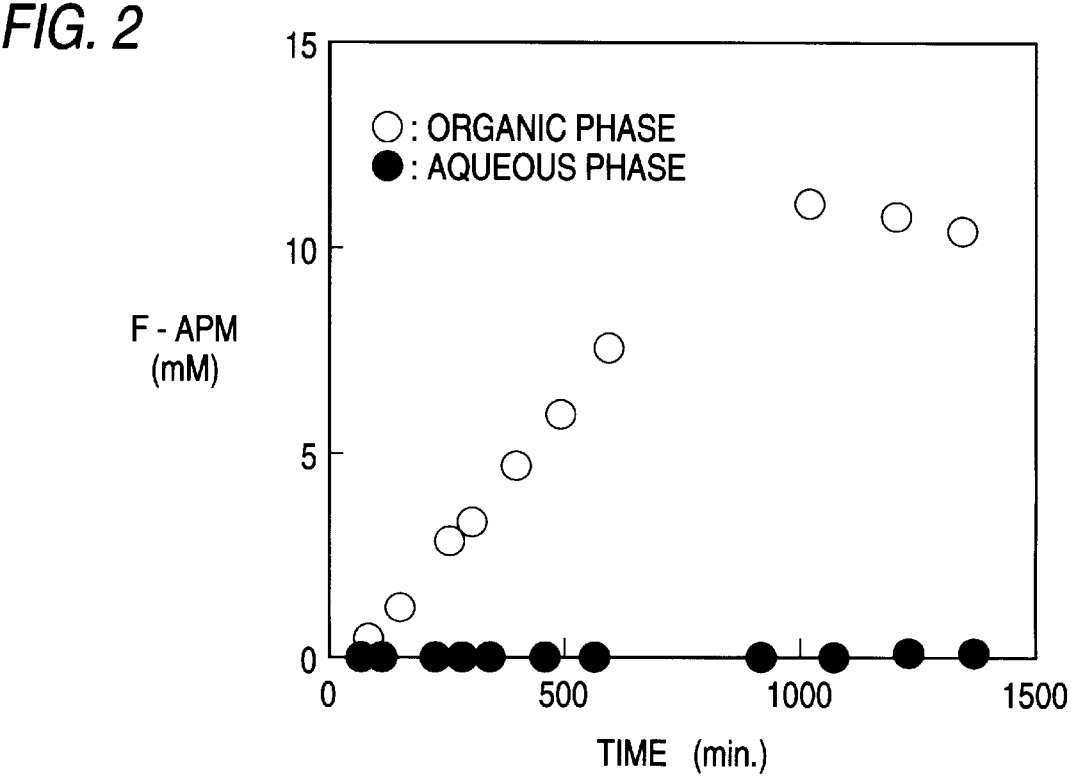
FIG. 2 shows changes of the concentrations of the F-APM produced in the aqueous phase and the organic phase with time.

FIG. 2 shows changes of the concentrations of F-L-APM with time in aqueous phase and organic phase.

It is clear that all F-APM produced were transferred to the organic phase and any F-APM did not remain in the aqueous phase, and the conversion ratio from F-L-Asp to F-APM based on F-L-Asp was about 12.6%.

COMPARATIVE EXAMPLE 1

The similar method to that of example 1 except for no use of organic solvent was carried out.

The conversion ratio from F-L-Asp to F-APM was only about 3.7%.

EXAMPLE 3

Figure 3:
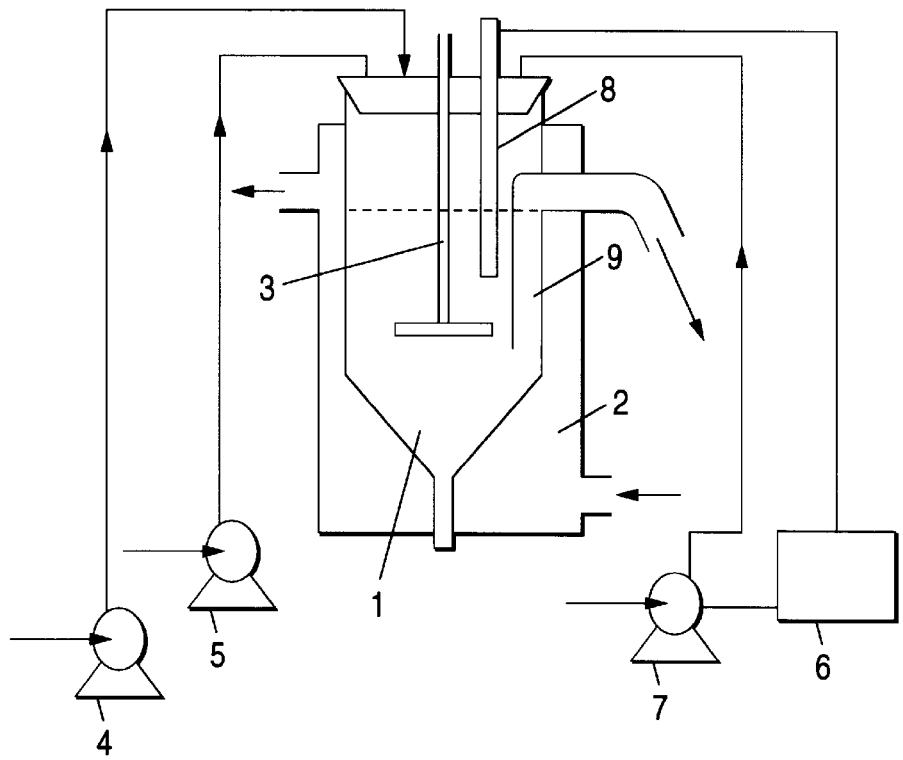
FIG. 3 shows a reactor for the continuous production of F-APM wherein figures shows following meanings.

An enzyme aqueous solution containing 20 g/l of thermoase (commercial name, manufactured by Daiwa Kasei Co., Ltd.) was poured previously into a reactor of 300 ml and substrate solutions of various organic solvents containing about 5 mM of F-L-Asp and about 130 mM of L-PM was supplied continuously to the reactor at 0.5 ml/min. (residence time in reactor was 10 hours) by use of reaction equipments described in FIG. 3.

Both starting materials of F-L-Asp and L-PM were extracted from the organic phase to the aqueous phase and were allowed to react aqueous phase containing free enzyme, and F-APM produced was extracted from the aqueous phase to the organic phase and F-APM was taken out continuously. The free enzymes did not have to be extracted from the aqueous phase because of their strong hydrophobic character, and the enzymes could be used continuously.

The reaction solution was stirred at 450 rpm by use of stirrer having bar-type blades of 3.5 cm of diameter and 7 mm of width, and temperature and pH were maintained at 40° C. and 6.0 during the reaction.

The conversion ratios to F-APM obtained by use of many kinds of organic solvents are showed in following Table 3.

TABLE 3

| Organic solvent | Conversion ratio to F-APM (%) |
|---|---|
| tri-butylphosphoric acid | 96 |
| methyl ethyl ketone | 64 |
| methyl ethyl ketone (D,L-PM was used) | 85 |
| 1-butanol | 82 |

It was shown in Table 3 that the conversion ratio in tylphosphoric acid was very high value of 96%.

FIG. 4 shows changes of the concentrations of the F-L-Asp, L-Pm and F-APM produced in the organic phase with time when tri-butylphosphoric acid was used, and indicate that F-APM was produced continuously at a constant concentration.

While the invention has been described in detail and with reference to specific examples thereof, it will be apparent to one skilled in the art that various changes and modifications can be made therein without departing from the spirit and scope thereof.

This application is based on application No. Hei 8-272129 filed in Japan on Oct. 15, 1996, the entire content of which is incorporated hereinto by reference.

What is claimed is:

1. An enzymatic method for producing N-formyl-α-L-aspartyl-L-phenylalanine methyl ester by a condensation reaction between N-formyl-L-aspartic acid and L-phenylalanine methyl ester or D,L-phenylalanine methyl ester, which comprises:

supplying an organic phase comprising a water-immiscible solvent containing N-formyl-L-aspartic acid and L- or D,L-phenylalanine methyl ester onto an aqueous phase comprising a thermolysin-like metalloprotease;

proceeding the condensation reaction in the aqueous phase to produce N-formyl-a-L-aspartyl-L-phenylalanine methyl ester; and extracting the N-formyl-α-L-aspartyl-L-phenylalanine methyl ester thus produced from the aqueous phase to the organic phase.

2. The method according to claim 1, wherein in the water-immiscible solvent the distribution ratio of N-formyl-α-L-aspartyl-L-phenylalanine methyl ester, $D_{F-APM}$, described by following equation (1) is $10^{-2}$ or more at pH=6.0:

$$D_{F-APM} = \frac{P_{F-APM}}{1 + 10^{pH-pK_{F-APM}}} \quad (1)$$

wherein $$P_{F-APM} = (C_{F-APM})_{org}/(C_{F-APM})_{aq} \quad (1a):$$

$$K_{F-APM} = \{(C_{F-APM^-})_{aq} \times C_{H^+}\}/(C_{F-APM})_{aq} \quad (1b);$$

which $(C_{F-APM})_{org}$: concentration of F-APM contained in the organic phase after the extraction of F-APM;

$(C_{F-APM})_{aq}$: concentration of F-APM remained in the aqueous phase after the extraction of F-APM;

$(C_{F-APM^-})_{aq}$: concentration of F-APM⁻ remained in the aqueous phase after the extraction of F-APM;

$C_{H^+}$: concentration of H⁺ remained in the aqueous phase.

3. The method according to claim 1, wherein in the water-immiscible solvent the distribution ratio of N-formyl-L-aspartic acid, $D_{F-L-Asp}$, described by following equation (2) is $10^{-4}$ or less at pH=6.0:

$$D_{F-L-Asp} = \frac{P_{F-L-Asp}}{1 + 10^{pH-pK_{F-L-Asp1}} + 10^{2pH-pK_{F-L-Asp1}-pK_{F-L-Asp2}}} \quad (2)$$

wherein $$P_{F-L-Asp} \ (C_{F-L-Asp})_{org}/(C_{F-L-Asp})_{aq} \quad (2a);$$

$$K_{F-L-Asp1} = \{(C_{F-L-Asp^-})_{aq} \times C_{H^+}\}/(C_{F-L-Asp})_{aq} \quad (2b);$$

$$K_{F-L-Asp2} = \{(C_{F-L-Asp^{2-}})_{aq} \times C_{H^+}\}/(C_{F-L-Asp^-})_{aq} \quad (2c);$$

which $(C_{F-L-Asp})_{org}$: concentration of F-L-Asp contained in the organic phase after the extraction of F-APM;

$(C_{F-L-Asp})_{aq}$: concentration of F-L-Asp remained in the aqueous phase after the extraction of F-APM;

$(C_{F-L-Asp^-})_{aq}$: concentration of F-L-Asp⁻ remained in the aqueous phase after the extraction of F-APM;

$C_{H^+}$: concentration of H⁺ remained in the aqueous phase after the extraction of F-APM;

$(C_{F-L-Asp^{2-}})_{aq}$: concentration of F-L-Asp²⁻ remained in the aqueous phase after the extraction of F-APM.

4. The method according to claim 1, wherein the water-immiscible solvent is at least one selected from the group consisting of tri-butylphosphoric acid, n-amylalcohol, methyl ethyl ketone, 1-butanol, isobutanol, and tertiary amylalcohol.

5. The method according to claim 1, wherein the water-immiscible solvent containing F-L-aspartic acid and L- or D,L-phenylalanine methyl ester is continuously supplied onto the aqueous phase, and organic phase comprising the N-formyl-α-L-aspartyl-L-phenylalanine methyl ester produced is continuously taken out.

6. The method according to claim 1, wherein N-formyl-L-aspartic acid and L-phenylalanine methyl ester or D,L-phenylalanine methyl ester are previously dissolved in the water-immiscible solvent, and then the organic phase comprising the water-immiscible solvent is supplied onto the aqueous phase.

7. The method according to claim 1, wherein solid N-formyl-L-aspartic acid and solid L-phenylalanine methyl ester or solid D,L-phenylalanine methyl ester are supplied to the organic phase and/or the aqueous phase separately.

* * * * *